United States Patent [19]
Thurwanger et al.

[11] Patent Number: 5,806,101
[45] Date of Patent: Sep. 15, 1998

[54] FACE ATTACHMENT ACCESSORY FOR PROTECTIVE CAPS

[75] Inventors: Gary J. Thurwanger, Springfield, Pa.; Timothy Bishop, Claymont, Del.

[73] Assignee: Fibre—Metal Products Co., Concordville, Pa.

[21] Appl. No.: 775,862

[22] Filed: Jan. 2, 1997

[51] Int. Cl.⁶ ........................................................ A42B 3/18
[52] U.S. Cl. ............................. 2/424; 2/9; 2/206; 2/420
[58] Field of Search .................................. 2/6.3, 6.5, 6.7, 2/8, 9, 206, 424, 418, 420, 10

[56] References Cited

U.S. PATENT DOCUMENTS 5,337,419   8/1994   Russell .......................................... 2/206

FOREIGN PATENT DOCUMENTS 1345851   11/1963   France .......................................... 2/8

*Primary Examiner*—Diana Biefeld
*Attorney, Agent, or Firm*—Connolly & Hutz

[57] ABSTRACT

An accessory such as a welding helmet is attached to a protective cap by means of a continuous band mounted to the inside of the accessory. The band is in the form of two pieces having overlapping ends which are adjustably connected together to accommodate different size protective caps. A hook structure may be provided on the band for hooking around the lower edge of the protective cap.

16 Claims, 3 Drawing Sheets

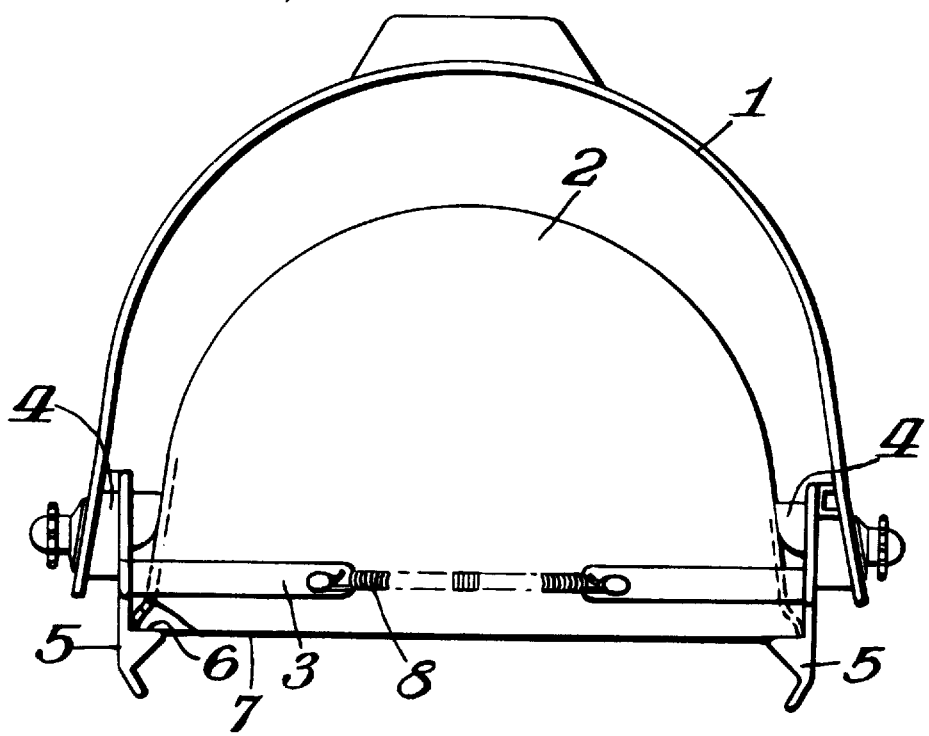
Fig.1(PriorArt)

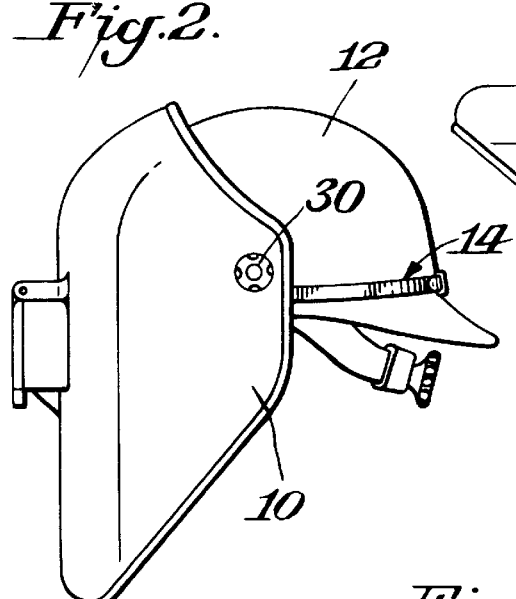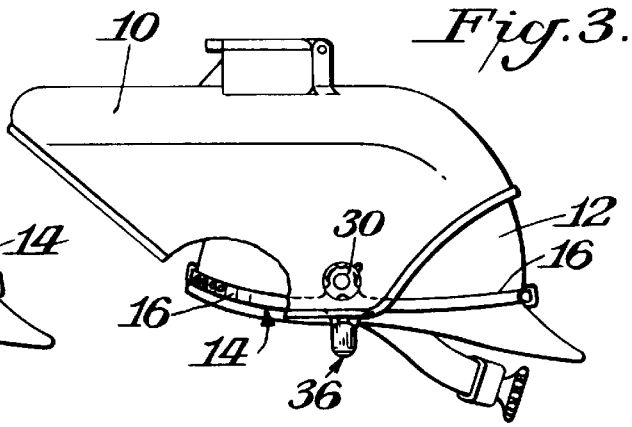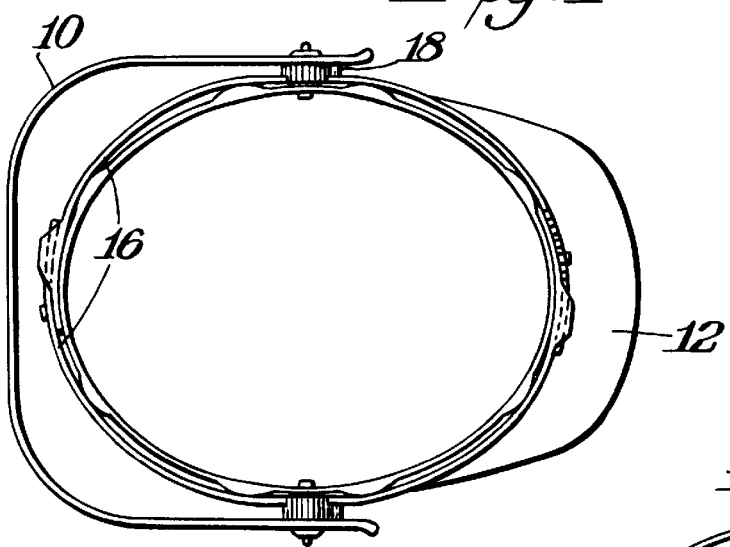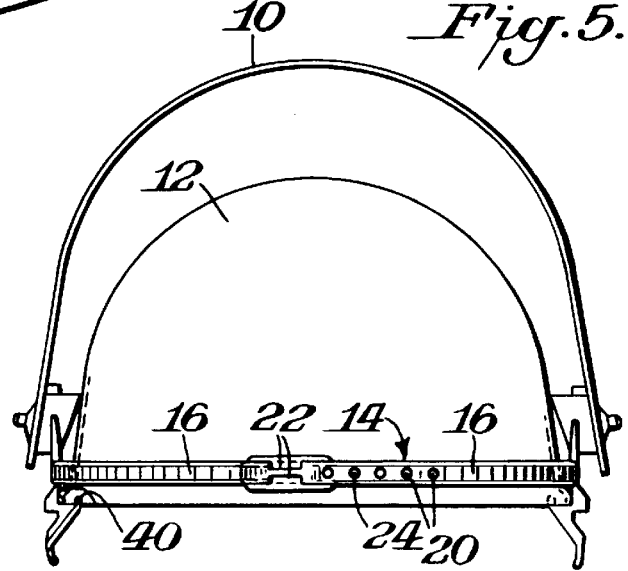

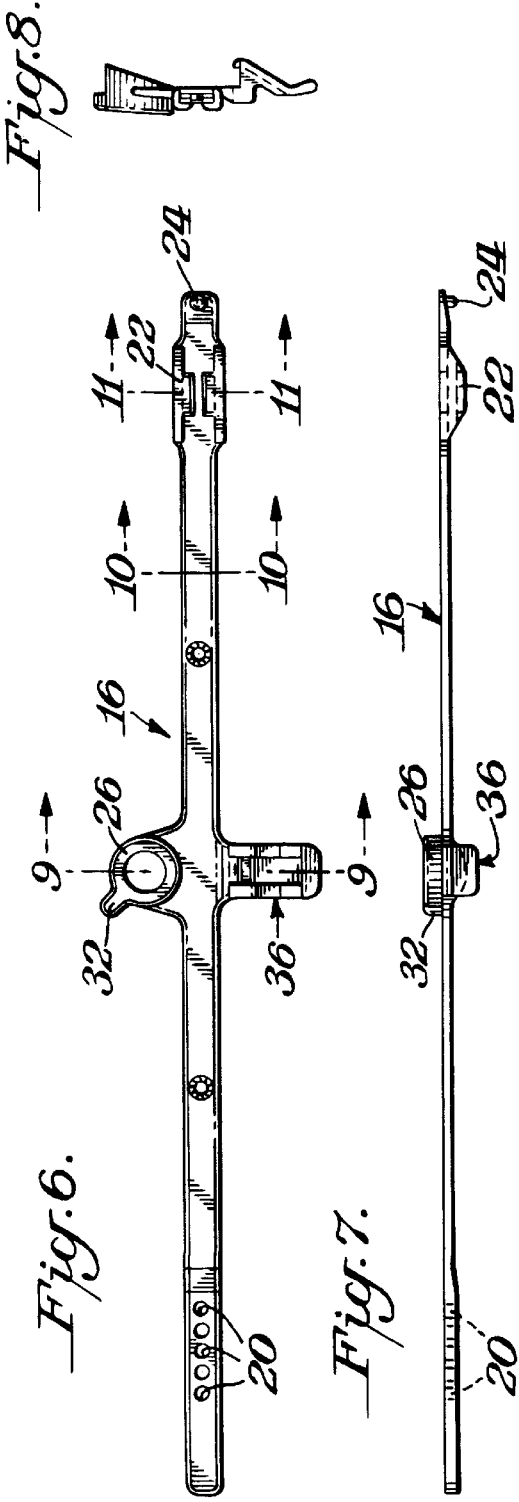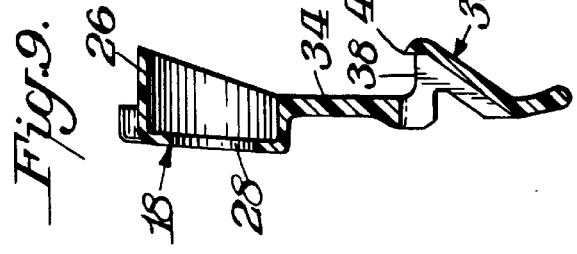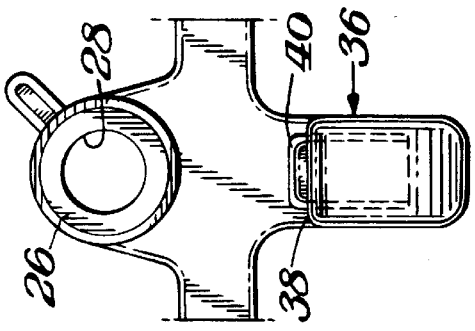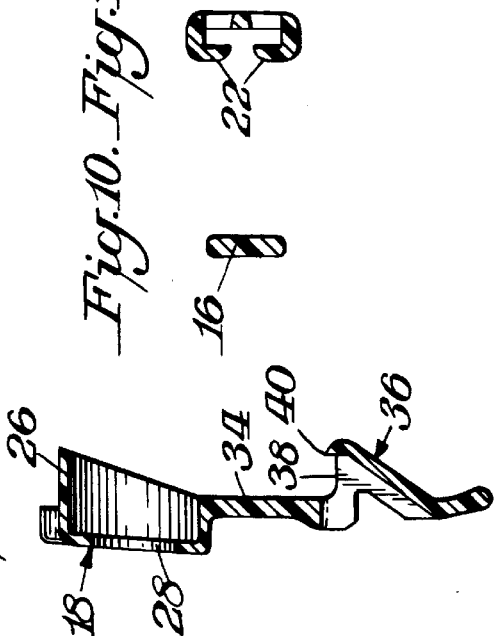

5,806,101

FACE ATTACHMENT ACCESSORY FOR PROTECTIVE CAPS

BACKGROUND OF THE INVENTION

Various types of face protection accessories are provided in the work place which are mounted to a protective cap or hard hat to protect the user's face and/or eyes in various work procedures. At times it is desired to remove the accessory, particularly from the field of vision. Such types of accessories include, for example, welding helmets, safety goggles and face shields which may be pivoted over the safety helmet or protective cap to a position out of the user's way when not in use.

A particularly useful and advantageous accessory marketed by Fibre-Metal Products Company involves providing a band on the inside of the accessory which would be mounted around the protective cap. The band includes a pivot arrangement to permit the accessory to be selectively disposed either in front of the user's face and/or eyes in its protective mode or up over the cap when it is not necessary to use the accessory. The band is formed of one piece plastic construction having spaced free ends which are interconnected by a spring to thereby provide a degree of adjustability in accommodating different size caps.

SUMMARY OF THE INVENTION

An object of this invention is to provide variations for the above noted band to assure a centering position regardless of what size cap is used by the wearer.

A further object of this invention is to provide a variation of the above noted band which assures a firm mounting of the band to the cap.

In accordance with this invention the band is made having overlapping free ends which overlap at diametrically opposite positions generally midway between the pivot connection of the band to the cap. The free ends are adjustably connected together so that when it is necessary to increase or decrease the overall length of the band such increase or decrease is accomplished by adjusting the degree of overlap of the free ends thereby controlling the effective length of each of the pieces on each side of the pivot connections to assure the desirable center position of the cap.

In a preferred practice of this invention the mounting assembly which secures the band to the cap includes a catch having a retainer lug which has a recessed or hooked shape to effectively grip the edge of the cap.

Preferably the band and its components are made of molded plastic material, thus avoiding the inclusion of any metal parts.

THE DRAWINGS

FIG. 1 is a rear elevational view of a prior art accessory band for mounting an accessory to a protective cap;

FIG. 2 is a side elevational view of an accessory mounted to a cap in accordance with this invention;

FIG. 3 is a view similar to FIG. 1 showing the accessory pivoted to the non-use position;

FIG. 4 is a bottom plan view of the arrangement shown in FIG. 2;

FIG. 5 is a rear elevational view of the arrangement shown in FIG. 2;

FIG. 6 is a side elevational view of one of the band pieces used in the arrangement shown in FIGS. 2–5;

FIG. 7 is a bottom plan view of the band piece shown in FIG. 6;

FIG. 8 is a right hand elevational view of the band piece shown in FIGS. 6–7;

FIGS. 9–11 are cross-sectional views taken through FIG. 6 along the lines 9—9, 10—10 and 11—11, respectively; and FIG. 12 is a fragmental rear elevational view of the band piece shown in FIGS. 6–8.

DETAILED DESCRIPTION

FIG. 1 illustrates an accessory mounting arrangement of the type marketed by Fibre-Metal Products Co. wherein an accessory such as a welding helmet 1 is mounted to a protective cap or hard hat 2 by means of a band 3 secured to the inner surface of helmet 1 by a pivot lock 4 which permits the helmet 1 to pivot to and from a face protecting position and a non-use position where the accessory is moved up over the hat. (See for comparison FIGS. 2–3.) A catch or lug 5 extends downwardly from band 3 and includes a flat shoulder 6 which rests against the lower edge 7 of the cap. The free ends of band 3 are interconnected by a spring 8 to permit the band to thereby accommodate different size caps.

Although the accessory mounting band of FIG. 1 is particularly effective, it does include features to which the present invention is directed for providing improvement type variations. In accordance with this invention an accessory 10 would be mounted to a cap 12 by means of a band 14 and would include many of the desirable features of the arrangement shown in FIG. 1. For example, the invention permits accessories, or face protection members such as welding helmets, safety goggles and face shields to be mounted to a cap and to permit the accessory to be pivoted up over the safety helmet or cap and thus be positioned out of the wearer's way when not in use. Such face protection members include a front section which would be selectively disposed in front of the face of a wearer with a pair of oppositely disposed sides connected to the front section. See FIGS. 2–5. The invention utilizes the advantages of this prior art in being able to easily mount and remove the band from the safety helmet or cap without the wearer either disassembling components or removing the protective cap or safety helmet from the user's head. The band does not require mounting blocks or slots on a safety helmet, thus avoiding the disadvantage of requiring tools to assemble and reducing electrical classification of a safety helmet. In addition, molded-on slots have the disadvantage of allowing falling objects to catch and transmit undesirable rotational forces to the wearer's head upon an impact.

The invention departs from the type of band shown in FIG. 1 in that it does not require any metal parts, such as spring 8, thus improving dielectric properties and reducing the possibility of the band scratching a safety helmet. The band can be assembled with significantly reduced assembly time and manufacturing costs. A significant departure of the band 14 of this invention, as compared to the band 3, is that the band 14 comprises two individual straps or pieces 16 each of which would be bent to a generally U-shape thus having two free ends. A free end from each piece 16 would be slidably disposed against or overlap a corresponding free end from the other piece 16. The overlapping would occur at the two diametrically opposite locations generally midway between the two pivot blocks 18. The two pivot blocks may be considered a first pivot assembly and a second pivot assembly.

FIGS. 6–12 illustrate the details of one of the pieces 16. As shown therein piece 16 is a generally flat strap having a plurality of holes 20 in one of its ends. Edge portions at the other end are bent over to form a guide sleeve 22. A pin 24 is located at the tip of the sleeve end. The end of the other piece having the holes 20 would slide into sleeve 22 and the pin 24 would be selectively inserted into one of the holes 20 of the other piece for securing the ends of the two pieces together. In this manner, it is possible to adjust the overall length of band 14 so as to accommodate different size caps or helmets.

The pivot block 18 is best illustrated in FIGS. 6, 9 and 12. As shown therein the pivot block includes a boss 26 having a central opening 28 through which a pivot pin having a threaded end would be inserted and would extend through the accessory 10 and locked in place by a fastener 30 threadably connected to the threaded pivot pin. (See FIGS. 2–3.) A stop member 32 extends outwardly for abutting against a complementary stop member on the inner surface of the accessory to limit the degree of pivotal movement of the accessory with respect to the band to position the accessory in its proper protective position or in its proper out of use position.

The accessory 10 is mounted to the cap 12 by means of the band extending around the outer surface of the cap as illustrated, for example, in FIGS. 2–5 and also by means of a locking arrangement secured to the band. FIGS. 5 and 9 best illustrate the details of the lock arrangement. As shown therein the band 16 has an integral downward extension 34 which includes a locking arrangement 36. The locking arrangement comprises a catch having hook structure in the form of a lug with a generally flat shoulder 38 and an upwardly extending lip 40 thereby forming a recess of hook type structure which fits around or snaps onto the lower edge of the cap 12. This differs from the arrangement shown in FIG. 1 where the lower edge of the cap simply rests on a flat shoulder.

Preferably, the strap pieces 16 are made of a molded plastic with each piece including integrally thereof the locking arrangement 36 and the pivot block 18. This permits assembly without any metal parts and significantly reduces assembly time and manufacturing costs. In addition, the absence of metal parts improves dielectric properties and reduces the possibility of the band scratching the cap. Moreover, the two piece design of the band allows the molder to assemble the piece parts at the molding press, thus further saving assembly costs.

The band 14 is designed to be adjustable to fit the wide range of cap sizes on the market. The use of the pin and hole arrangement at either end allows the pivot point of an accessory to be positioned exactly into the desirable center position of a safety helmet or cap. This adjustment to fit any size protective cap allows the user to position the accessory to optimize viewing area while reducing tunnel vision. The band itself functions as a spring, thus replacing the metal spring shown in FIG. 1. The catch piece 36 at the base of the pivot lug provides a better grip to the edge of the safety helmet or cap when the band 14 is snapped over it. Another feature of the band is that it reduces the amount that an accessory must spread in order to clear the mounting mechanism of a safety cap. This allows the accessory to fit and function better over the whole range of varying widths of safety cap models.

The band itself would form a unit which is separate from the accessory, but which would include various structure such as the pivot block that enables the unit to be mounted to an accessory. Thus, various types or sizes, colors, etc. of bands might be provided for use with different accessories.

It is to be understood that although the various figures illustrate the accessory as being in the form of a welding helmet, the term "accessory" is intended to include other types of protective members such as, but not limited to, safety goggles and face shields where generally what is intended is to provide a member which protects the user's face and/or eyes and which may be moved to a position of non-use when desired. Such accessories generally include a front facial section having oppositely disposed side sections with the band secured to its inner surface for mounting to the cap.

What is claimed is:

1. A face attachment accessory for use with a rigid protective cap comprising, in combination, a face protection member having a front section for being selectively disposed in front of the face of a wearer, said face protection member having a pair of oppositely disposed sides connected to said front section, a continuous band mounted to the inside of said face protection member, a locking structure on said band for the detachable mounting of said band to the protective cap, said band being mounted to said face protection member by a pivot assembly to permit said face protection member to be selectively pivoted about the protective cap to a first position disposed in front of and protecting the face of a wearer and to a second position away from the face of a wearer, said continuous band being formed from two band pieces of generally equal length having two sets of overlapping free ends, and a connecting assembly at each of said sets of free ends to comprise a pair of connecting assemblies adjustably connecting each set of said free ends together to permit the overall length of said band to be varied for accommodating different size protective caps.

2. The accessory of claim 1 wherein said band includes a pair of diametrically opposite locking arrangements for detachable mounting to the lower edge of the cap, and each of said locking arrangements including a hook structure.

3. The accessory of claim 2 wherein said pivot assembly is a first pivot assembly, a second pivot assembly spaced from said first pivot assembly further mounting said band to said face protection member, each of said connecting assemblies being disposed generally midway between said first pivot assembly and said second pivot assembly, and each said pivot being connected to a different band piece.

4. The accessory of claim 1 wherein said pivot assembly is a first pivot assembly, a second pivot assembly spaced from said first pivot assembly further mounting said band to said face protection member, said free ends of said pieces overlapping at diametrically opposite portions located generally midway between said first pivot assembly and said second pivot assembly.

5. A face attachment accessory for use with a rigid protective cap comprising, in combination, a face protection member having a front section for being selectively disposed in front of the face of a wearer, said face protection member having a pair of oppositely disposed sides connected to said front section, a continuous band mounted to the inside of said face protection member, a locking structure on said band for the detachable mounting of said band to the protective cap, said band being mounted to said face protection member by a first pivot assembly and a second pivot assembly to permit said face protection member to be selectively pivoted about the protective cap to a first position disposed in front of and protecting the face of a wearer and to a second position away from the face of a wearer, said continuous band being formed from two band pieces having two sets of overlapping free ends, a connecting assembly at each of said sets of free ends to comprise a pair of connecting assemblies adjustably connecting each set of said free ends together to permit the overall length of said band to be varied for accommodating different size protective caps, said locking structure including a pair of diametrically opposite locking arrangements for detachable mounting to the lower edge of the cap, each of said locking arrangements including a hook structure, said second pivot assembly being spaced from said first pivot assembly for mounting said band to said face protection member at spaced locations, each of said connecting assemblies being disposed generally midway between said pivot assemblies, and said hook structure comprising a lug having a flat shoulder and terminating in an upstanding lip.

6. The accessory of claim 5 wherein each of said pieces has a plurality of holes at one of its ends and a pin at the other of its ends for selective engagement in said holes of the other of said pieces.

7. The accessory of claim 6 wherein each of said pieces includes an integral sleeve into which the free end of the other of said pieces having said holes may be inserted.

8. The accessory of claim 7 wherein said band is made of non-metallic material.

9. The accessory of claim 8 wherein said non-metallic material is molded plastic.

10. The accessory of claim 9, in further combination with a protective cap, said face protection member being a welding helmet, and said accessory and said helmet being mounted to said cap.

11. The accessory of claim 9, in further combination with a protective cap, said accessory being safety goggles, and said accessory and said goggles being mounted to said cap.

12. The accessory of claim 9, in further combination with a protective cap, said accessory being a face shield, and said accessory and said shield being mounted to said cap.

13. A face attachment accessory for use with a rigid protective cap comprising, in combination, a face protection member having a front section for being selectively disposed in front of the face of a wearer, said face protection member having a pair of oppositely disposed sides connected to said front section, a continuous band mounted to the inside of said face protection member, a locking structure on said band for the detachable mounting of said band to the protective cap, said band being mounted to said face protection member by a pivot assembly to permit said face protection member to be selectively pivoted about the protective cap to a first position disposed in front of and protecting the face of a wearer and to a second position away from the face of a wearer, said continuous band being formed from two band pieces having two sets of overlapping free ends, a connecting assembly at each of said sets of free ends to comprise a pair of connecting assemblies adjustably connecting each set of said free ends together to permit the overall length of said band to be varied for accommodating different size protective caps, and each of said pieces having a plurality of holes at one of its ends and a pin at the other of its ends for selective engagement in said holes of the other of said pieces.

14. The accessory of claim 13 wherein each of said pieces includes an integral sleeve into which the free end of the other of said pieces having said holes may be inserted.

15. The accessory of claim 14 wherein said band is made of non-metallic material.

16. A face attachment accessory for use with a rigid protective cap comprising, in combination, a face protection member having a front section which may be selectively disposed in front of the face of a wearer, said face protection member having a pair oppositely disposed sides connected to said front section, a continuous band mounted to the inside of said face protection member, a locking structure on said band for the detachable mounting of said band to the protective cap, said band being mounted to said face protection member by a pivot assembly to permit said face protection member to be selectively pivoted about the protective cap to a first position disposed in front of and protecting the face of a wearer and to a second position away from the face of a wearer, and said locking structure comprising a lug integral with and depending from said band, and said lug having a flat shoulder and an upstanding lip at the outer edge of said flat shoulder to form a hook structure for fitting around the lower edge of the cap.

* * * * *